United States Patent [19]
Marchessault et al.

[11] Patent Number: 6,146,665
[45] Date of Patent: Nov. 14, 2000

[54] ENTRAPMENT OR MICROENCAPSULATION OF DRUGS IN A POLYHYDROXYALKANOATE FORMED BY ENZYME SYNTHESIS

[75] Inventors: Robert H. Marchessault; Dusica Maysinger, both of Montreal, Canada; Geoffrey Alan Ralph Nobes, El Cerrito, Calif.

[73] Assignee: McGill University, Montreal, Canada

[21] Appl. No.: 09/150,019

[22] Filed: Sep. 9, 1998

[51] Int. Cl.[7] .............................. A61K 9/16; A61K 9/14; A61K 9/50; C12P 7/62; C12N 11/04
[52] U.S. Cl. .................... 424/497; 424/489; 435/135; 435/182
[58] Field of Search ..................... 424/497, 489, 424/491; 435/41, 135, 182

[56] References Cited

U.S. PATENT DOCUMENTS

| | | | |
|---|---|---|---|
| 5,229,279 | 7/1993 | Peoples et al. | 435/135 |
| 5,250,430 | 10/1993 | Peoples et al. | 435/232 |
| 5,451,456 | 9/1995 | Marchessault et al. | 428/327 |

OTHER PUBLICATIONS

Juni, et al., Journal of Controlled Release, vol. 4, 1986, pp. 25–32.
Kawaguchi, et al., Journal of Pharmaceutical Sciences, vol. 81, No. 6, Jun. 1992, pp. 508–512.
Bissery, et al., Microspheres and Drug Therapy Pharmaceutical, Immunological and Medical Aspects, 1984, pp. 217–227, edited by S.S. Davis et al, Elsevier Science Publishers.

*Primary Examiner*—David M. Naff
*Attorney, Agent, or Firm*—Swabey Ogilvy Renault

[57] ABSTRACT

A hydrophilic or lipophilic drug is entrapped or microencapsulated in a polyhydroxyalkanoate homopolymer or copolymer. The homopolymer or copolymer is synthesized in an aqueous medium containing a dissolved hydrophilic drug by in vitro enzyme polymerization of a hydroxyalkanoate Coenzyme A monomer to form microporous granules entrapping the drug. The enzyme may be a polyhydroxyalkanoate synthase, and the monomer may be 3-hydroxybutyryl Coenzyme A or 3-hydroxyvalerate Coenzyme A. The monomer is produced by reaction of a carboxylic acid group of a hydroxyalkanoic acid with a thiol group of Coenzyme A. To microencapsulate a lipophilic drug, droplets of oil containing a lipophilic drug are formed dispersed in an aqueous medium such as in the form of an oil-in-water emulsion. The polyhydroxyalkanoate homopolymer or copolymer is formed in the aqueous medium by the enzyme polymerization to form microcapsules having a core of oil containing the drug. The granules or microcapsules containing the drug may be dried.

10 Claims, 1 Drawing Sheet

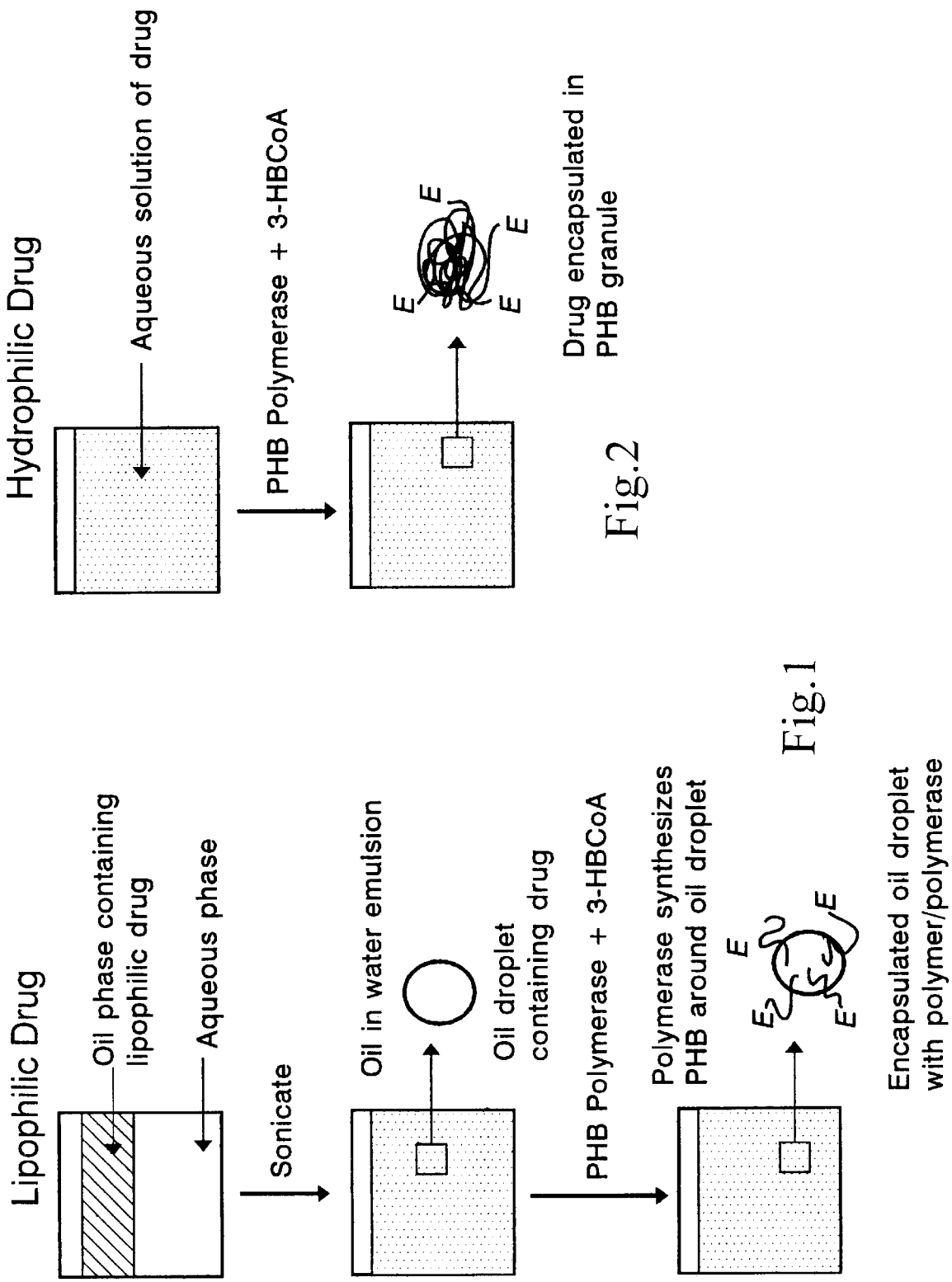

ENTRAPMENT OR MICROENCAPSULATION OF DRUGS IN A POLYHYDROXYALKANOATE FORMED BY ENZYME SYNTHESIS

BACKGROUND OF THE INVENTION i) Field of the Invention

This invention relates to a process for producing an entrapped or microencapsulated drug, more especially a process employing in vitro synthesis of a polyhydroxyalkanoate homopolymer or copolymer.

ii) Description of Prior Art Poly(hydroxyalkanoates), PHA, are biopoly(β-hydroxyalkanoate)-esters which are produced by microorganisms. The general pathways of PHA biosynthesis are well known. The poly(β-hydroxybutyrate) (PHB) biosynthetic pathway uses acetyl-CoA which generates [R]-(−)-3-hydroxybutyryl-CoA as the natural monomer. This monomer responds to the naturally produced polymerase enzyme which rapidly produces PHB.

Processes have been proposed for encapsulating drugs within a polyhydroxyalkanoate shell. These processes typically require use of organic solvents, see for example Bissery et al, Microspheres and Drug Therapy Pharmaceutical, Immunological and Medical Aspects, edited by S. S. Davis et al, Elsevier Science, pp. 217–227, 1984; Juni et al Journal of Controlled Release, 4, 25–32, 1986; and Kawaguchi et al, Journal of Pharmaceutical Sciences, 81, 508–512, 1992. Use of polyhydroxyalkanoates in the entrappment or microencapsulation of drugs is especially advantageous since these polymers are biodegradable, non-toxic and otherwise non-harmful when administered to a living body.

It would be desirable to provide new entrappment or encapsulation processes employing non-toxic, biodegradable polymers, especially polymers that can be formed in situ in the entrappment or encapsulation of the drug.

SUMMARY OF THE INVENTION

It is an object of this invention to provide a process for producing an entrapped or microencapsulated drug.

It is a particular object of this invention to provide such a process for the entrappment of hydrophilic drugs.

It is a further particular object of this invention to provide such a process for the microencapsulation of lipophilic drugs.

In accordance with the invention there is provided a process for producing an entrapped or microencapsulated drug comprising: providing a drug in an aqueous medium, synthesizing a polyhydroxyalkanoate homopolymer or copolymer in said aqueous medium by in vitro enzyme polymerization of at least one hydroxyalkanoate-Coenzyme A monomer precursor of said polyhydroxyalkanoate, with formation in said aqueous medium of microporous granules or microcapsules of the synthesized polyhydroxyalkanoate entrapping or microencapsulating fluid from said medium, containing said drug, and recovering said granules or microcapsules from said aqueous medium.

DETAILED DESCRIPTION OF THE INVENTION i) Polyhydroxyalkanoate Homopolymer and Copolymers The polyhydroxyalkanoate homopolymers and copolymers are derived from hydroxyalkanoates of 3 to 14 carbon atoms. The homopolymers are based on a single hydroxyalkanoate, and the copolymers are based on two different hydroxyalkanoates.

The preferred hydroxyalkanoates are the 3-hydroxybutyrates and the 3-hydroxyvalerates. The preferred homopolymers are derived from the 3-hydroxybutyrates, namely, poly(β-hydroxybutyrate), i.e., PHB; the preferred copolymers are derived from 3-hydroxybutyrate and 3-hydroxyvalerate, namely, poly(3-hydroxybutyrate-co-3-hydroxyvalerate) i.e., P(3HB-3HV).

The homopolymers and copolymers derived from hydroxyalkanoates in accordance with the invention are non-toxic and biodegradable. For example, poly(3-hydroxybutyrate) degrades to (D)-3-hydroxybutyric acid which is a normal constituent of human blood being produced during fatty acid oxidation in the liver. Complete degradation in the environment leads to $Co_2$ and $H_2O$.

The PHB homopolymer is brittle so that in some situations there may be a preference for the P(3HB-3HV) copolymer which is more ductile. Suitable copolymers may contain 10 to 15%, preferably 11 to 13%, by weight, of 3 hydroxyvalerate.

The preferred alkanoates are the R-(−)-3-hydroxyalkanoic acids and the homopolymers and copolymers produced by the in vitro synthesis of the invention having a weight average molecular weight of $10 \times 10^6$ to $1.3 \times 10^7$. The homopolymers and copolymers produced by the in vitro synthesis are non-pathways are described by Jackson et al Annals of the New York Academy of Sciences, 745, (Biochem. Eng. VIII) 134–148, 1994. Representative bacteria for the in vivo biosynthesis are *Alcaligenes entrophus, Rhodospirillum rubrum, Pseudomonas oleovorans* and *Pseudomonas aeruginosa*. In each case the polymerization is catalyzed by a PHA synthase, also referred to as PHA polymerase and the substrate monomer is a hydroxyacyl-Coenzyme A, in which the acyl corresponds to the desired alkanoate.

Recently an in vitro synthesis has been employed which does not require the bacteria employed in the biosynthesis.

The in vitro synthesis employs the synthetically produced hydroxy acyl-Coenzyme A substrate monomer and a polyhydroxyalkanoate polymerase expressed from an isolated structured gene; for example, the polymerase may be encoded by a gene which is expressed naturally by *Alcaligenes eutrophus* or *Pseudomonas oleovorans*.

The genes encoding the polyhydroxyalkanoate polymerase which occur naturally in PHA producing bacteria such as *Alcaligenes eutrophus* have been identified and isolated and expressed in a non-PHA producing organism, *E. coli*. The modified *E. coli* does not produce PHA but does produce the polyhydroxyalkanoate polymerase. This polymerase is employed in the in vitro synthesis of PHA illustrated in Equation (I) below for the in vitro synthesis of poly(3-hydroxybutyrate):

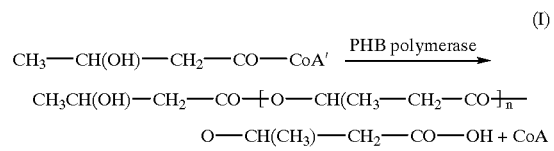

(I)

in which n is an integer of the order of 200,000 to 150,000 and CoA' refers to the mercapto radical formed by removing hydrogen from the thiol of the thioethylamino of Coenzyme A. Coenzyme A is a well established co-factor in enzymatic acetyl transfer reactions and is described with formula in The Merck Index, Eleventh Edition, published by Merck & Co. Inc. 1989, entry No. 2465 at pages 385–386 incorporated hereby by reference. Coenzyme A is a molecule which can be considered to be built up from pantetheine, adenosine and phosphoric acid, the empirical formula is $C_{21}H_{36}N_7O_{16}P_3S$ and the chemical formula is:

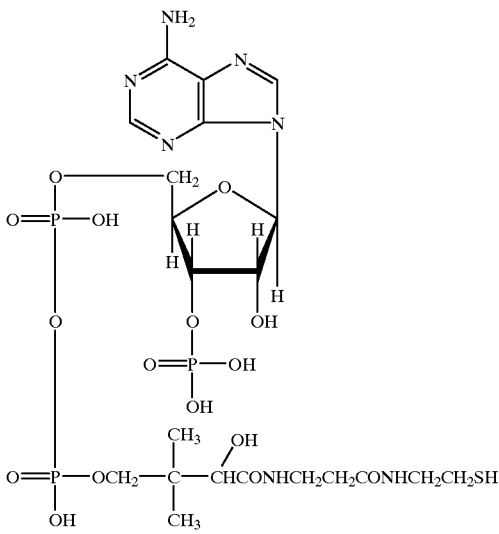

The production of polyhydroxyalkanoate polymerase for use in the in vitro present invention is described in U.S. Pat. No. 5,229,279, Anthony Sinskey et al, issued Jul. 20, 1993 and U.S. Pat. No. 5,250,430, Anthony Sinskey et al, issued Oct. 5, 1993, the teachings of both of which are incorporated herein by reference. Furthermore, polyhydroxybutyrate polymerase produced by the procedures described in the two U.S. Patents is available from Metabolix Inc. of Cambridge, Mass., U.S.A.

The monomer substrate employed in the in vitro process of the invention is produced by chemical reaction between Coenzyme A and the appropriate hydroxyalkanoic acid, the reaction being an esterification type reaction between the carboxylic acid group of the hydroxyalkanoic acid and the thiol group of the Coenzyme A.

The in vitro synthesis of the invention is carried out in an aqueous medium containing the drug to be microencapsulated by the in vitro synthesized homopolymer or copolymer.

Typically a phosphate buffer and the synthetic 3-hydroxyalkanoate-CoA are introduced into the aqueous medium and the polymerization is initiated by the addition of the polyhydroxyalkanoate polymerase. The synthesis may be followed spectrophotometrically, following a 200-fold dilution, by monitoring the disappearance of the 3-hydroxyalkanoate-CoA and the release of free CoA, by following the absorptions at 260 and 236 nm. Typically the reaction is completed in about 2 hours. The free Coenzyme A is recovered and may be employed to synthesize fresh 3-hydroxyalkanoate-CoA monomer substrate for polymerization.

The formed granules or microcapsules are recovered from the aqueous medium and dried.

In the in vitro synthesis the average granule or microcapsule diameter, particle size distribution and volume increase with reaction time; the average granule or microcapsule size increases rapidly initially, especially during the first 20 minutes of reaction.

Since the in vitro synthesis is free of components present in the bacterial cell in the in vivo synthesis, for example, lipids and proteins, the granule or microcapsule size is significantly larger than achieved in in vivo synthesis and additionally coagulation occurs early in the reaction. In the in vivo synthesis bacterial cell components such as lipids and proteins stabilize the granules against coagulation.

iii) Hydrophilic Drugs

In the case of hydrophilic drugs, for example, netilmicin and dopamine (α-methyldopa), the drugs are dissolved in the aqueous medium, which then forms the aqueous medium for the in vitro synthesis. In this case the in vitro synthesis produces polymer particles which coalesce to microporous granules which entraps the aqueous medium containing the micropores.

In particular, the synthesized polymer particles are allowed to coalesce to form the microporous granules, and the granules are recovered with aqueous medium and dissolved drug entrapped in the micropores of the microporous granules. The granules are dried with the entrapped drug therein.

iv) Lipophilic Drugs

In the case of lipophilic drugs, for example, progesterone, the drugs are dissolved in an oil, which is then emulsified or dispersed in an aqueous medium as an oil-in-water emulsion or dispersion. The aqueous medium forms an aqueous phase containing droplets of the oil and the drug is contained in the oil droplets. In this case the in vitro synthesized polymer forms a microcapsule wall or shell about a fluid core, the fluid core being of the oil containing the dissolved lipophilic drug. The formed microcapsules are recovered from the aqueous phase and dried.

BRIEF DESCRIPTION OF DRAWINGS

FIG. 1 illustrates schematically entrappment of a lipophilic drug by a process of the invention, and FIG. 2 illustrates schematically microencapsulation of a hydrophilic drug by a process of the invention.

DESCRIPTION OF PREFERRED EMBODIMENTS WITH REFERENCE TO THE DRAWINGS

With further reference to FIG. 1, there is shown schematically a flow diagram for the microencapsulation of a lipophilic drug such as progesterone by the in vitro synthesis of poly(3-hydroxybutyrate) in accordance with the invention.

The lipophilic drug is dissolved in an oil phase. An aqueous phase is added to the oil phase and the two phases are sonicated to produce an oil-in-water emulsion in which the dispersed or emulsified oil droplets contain the drug. The 3-hydroxybutyrate-Coenzyme A and the polyhydroxybutyrate polymerase are added to the emulsion where they enter the aqueous phase and poly(3-hydroxybutyrate) is synthesized around the oil droplets. The encapsulated oil droplets are then removed from the emulsion and dried to provide microcapsules having a shell of the poly(3-hydroxybutyrate) and a fluid core comprising the oil with the lipophilic drug dissolved therein. It will be understood that the oil should be one suitable for oral administration to a human, for example, a vegetable oil such as olive oil.

With further reference to FIG. 2, there is shown a flow sheet for the production of polymer granules for entrappment of a hydrophilic drug such as dopamine.

The hydrophilic drug is dissolved in an aqueous medium to form an aqueous solution of the drug. The 3-hydroxybutyrate-Coenzyme A and the polyhydroxybutyrate polymerase are added to the aqueous solution, the poly(3-hydroxybutyrate) is synthesized within the aqueous solution as granules which coalesce forming a microporous granule which entraps the aqueous solution in the micropores. In this way there are produced polymer granules entrapping a fluid comprising the drug in aqueous solution. The polymer granules are removed from the aqueous solution and dried.

The in vitro synthesis of the invention may be characterized as a precipitation polymerization or pseudoemulsion polymerization.

EXAMPLES

Example 1

Netilmicin, a water soluble antibiotic, was assayed according to Emit procedure. To three test tubes a constant volume of 3 aqueous solutions of netilmicin were added, namely, aqueous solutions of 34 micrograms per litre, 5.0 micrograms per litre and 3.0 micrograms per litre of netilmicin. To each test tube was added a constant amount of PHB polymerase and 3-hydroxybutyrate-Coenzyme A monomer substrate and the reaction was allowed to proceed overnight. After centrifugation to remove the PHB in vitro particles with their content of netilmicin, an assay of the netilmicin and the supernatant was made. From the results it was found that 17%, 4.1% and 2.1% of the total initial netilmicin was entrapped in the in vitro particles.

Example 2

The Netilmicin Emit assay was used. To 3 Eppendorf centrifuge tubes each containing 1 mg of netilmicin dissolved in water were added 1 micro litre, 2 micro litres and 5 micro litres of PHB polymerase solution and the same amount of substrate monomer solution (3-hydroxybutyrate-Coenzyme A). After standing overnight the tubes were centrifuged at 14,000 rpm for 10 minutes and the supernatant was assayed for netilmicin. In addition, the pellets in the centrifuge tubes were dissolved in 300 micro litres of chloroform and 500 micro litres of water. The pellets were found to contain 0.42%, 1.2% and 4.5% of the total initial netilmicin.

Example 3

A radio-labelled lipophilic steroid drug (tritiated progesterone) was dissolved in olive oil and an excess of water was added to create an oil-in-water emulsion. PHB polymerase and monomer substrate (3-hydroxybutyrate-Coenzyme A) were added to the emulsion with gentle stirring. After allowing the reaction to proceed overnight a suspension of particles was obtained. The particles were hardened by adding an aqueous polyvinyl alcohol solution with stirring, and the suspension was collected on a Millipore (Trade-mark) filter. Analytical radioassay showed that steroid and PHN were predominantly present in the solid collected on the filter.

We claim:

1. A process for producing an entrapped drug comprising:
    providing a hydrophilic drug dissolved in an aqueous medium,
    synthesizing a polyhydroxyalkanoate homopolymer or copolymer in said aqueous medium by in vitro enzyme polymerization of at least one hydroxyalkanoate Coenzyme A monomer produced by reaction of a carboxylic acid group of a hydroxyalkanoic acid with a thiol group of Coenzyme A, said at least one monomer being a precursor of said polyhydroxyalkanoate, with formation in said aqueous medium of microporous granules of the synthesized polyhydroxyalkanoate entrapping dissolved drug, and
    recovering said granules from said aqueous medium.

2. A process according to claim 1, wherein said precursor monomer is selected from 3-hydroxybutyryl-Coenzyme A, 3-hydroxyvalerate-Coenzyme A and mixtures thereof, and said enzyme polymerization is catalyzed by a corresponding polyhydroxyalkanoate synthase.

3. A process according to claim 1, wherein said precursor monomer is (R)-(-)-3-hydroxybutyryl-Coenzyme A and said synthesized polyhydroxyalkanoate is a polyhydroxybutyrate homopolymer.

4. A process for producing a microencapsulated drug comprising:
    providing droplets of oil containing a lipophilic drug, said droplets being dispersed in an aqueous medium,
    synthesizing a polyhydroxyalkanoate homopolymer or copolymer in said aqueous medium by in vitro enzyme polymerization of at least one hydroxyalkanoate Coenzyme A monomer produced by reaction of a carboxylic acid group of a hydroxyalkanoic acid with a thiol group of Coenzyme A, said at least one monomer being a precursor of said polyhydroxyalkanoate, with formation in said aqueous medium of microcapsules having a capsule wall of the synthesized polyhydroxyalkanoate microencapsulating a fluid core comprising said oil containing said drug, and
    recovering said microcapsules from said aqueous medium.

5. A process according to claim 4, wherein said precursor monomer is (R)-(-)-3-hydroxybutyryl-Coenzyme A and said synthesized polyhydroxyalkanoate is a polyhydroxybutyrate homopolymer.

6. A process according to claim 4, wherein said precursor monomer is selected from 3-hydrokybutyryl-Coenzyme A, 3-hydroxyvalerate-Coenzyme A and mixtures thereof, and said enzyme polymerization is catalyzed by a corresponding polyhydroxyalkanoate synthase.

7. A process for producing drug entrapped granules comprising:
    dissolving a hydrophilic drug in an aqueous medium,
    synthesising a polyhydroxyalkanoate homopolymer or copolymer in said aqueous medium by in vitro enzyme polymerization of at least one hydroxyalkanoate Coenzyme A monomer produced by reaction of a carboxylic acid group of a hydroxyalkanoic acid with a thiol group of Coenzyme A, said at least one monomer being a precursor of said polyhydroxyalkanoate, with formation in said aqueous medium of particles of the synthesized polyhydroxyalkanoate,
    allowing said particles to coalesce to microporous granules having aqueous medium containing dissolved hydrophilic drug entrapped in micropores of the granules,
    recovering said microporous granules with said aqueous medium and dissolved hydrophilic drug entrapped in the micropores of said microporous granules, and
    drying said granules with said entrapped hydrophilic drug.

8. A process according to claim 7, wherein said precursor monomer is (R)-(-)-3-hydroxybutyryl-Coenzyme A and said synthesized polyhydroxyalkanoate is a polyhydroxybutyrate homopolymer.

9. A process for producing a microencapsulated lipophilic drug comprising:
    dissolving a lipophilic drug in an edible oil, adding an aqueous medium and forming an oil-in-water emulsion comprising droplets of said oil containing the dissolved lipophilic drug, in an aqueous phase, synthesizing a polyhydroxyalkanoate homopolymer or copolymer in said aqueous phase by in vitro enzyme polymerization of at least one hydroxyalkanoate Coenzyme A monomer produced by reaction of a carboxylic acid group of a hydroxyalkanoic acid with a thiol group of Coenzyme A, said at least one monomer being a precursor of said polyhydroxyalkanoate, with formation in said aqueous phase of microcapsules having a capsule wall of the synthesized polyhydroxyalkanoate entrapping a fluid core comprising said oil with said drug dissolved therein, recovering said microcapsules, and drying said microcapsules with said fluid core therein.

10. A process according to claim 9, wherein said precursor monomer is (R)-(−)-3-hydroxybutyryl-Coenzyme A and said synthesized polyhydroxyalkanoate is a polyhydroxybutyrate homopolymer.

* * * * *